US00PP29641P3

(12) United States Plant Patent
Van Swieten

(10) Patent No.: US PP29,641 P3
(45) Date of Patent: Sep. 4, 2018

(54) ***PHALAENOPSIS* ORCHID PLANT NAMED 'PHALDILEP'**

(50) Latin Name: ***Phalaenopsis* hybrid**
Varietal Denomination: PHALDILEP

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 30 days.

(21) Appl. No.: 15/530,069

(22) Filed: Nov. 30, 2016

(65) Prior Publication Data

US 2018/0153076 P1 May 31, 2018

(51) Int. Cl.
*A01H 5/02* (2018.01)

(52) U.S. Cl.
USPC ..... Plt./311
CPC ..... *A01H 5/02* (2013.01)

(58) Field of Classification Search
USPC ..... Plt./311
See application file for complete search history.

*Primary Examiner* — Keith O. Robinson
(74) *Attorney, Agent, or Firm* — Jondle & Associates, P.C.

(57) ABSTRACT

A new and distinct variety of *Phalaenopsis* plant named 'PHALDILEP', particularly characterized by having white flowers with a small purple center and dark purple lip, 1 to 3 peduncles that are medium long and sturdy, leaves that are oblong, and is propagated by meristem tissue culture, is disclosed.

3 Drawing Sheets

Genus and species: *Phalaenopsis* hybrid.
Variety denomination: 'PHALDILEP'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALDILEP'.

The new *Phalaenopsis* plant is a product of a planned breeding program conducted by the inventor in Bleiswijk, The Netherlands. The objective of this breeding program was to create a new *Phalaenopsis* plant with unique white flowers with a small purple center and dark purple lip, suitable for potted plant production.

The new *Phalaenopsis* plant 'PHALDILEP' is a result of cross-pollination made by the inventor in October 2001 in Bleiswijk, The Netherlands of the proprietary female, or seed parent, *Phalaenopsis* hybrid '01-1401' (unpatented) with the proprietary male, or pollen parent, *Phalaenopsis* hybrid '01-1402' (unpatented).

The new *Phalaenopsis* was selected by the inventor as a single plant within the progeny of the stated cross-pollination in a controlled greenhouse in Bleiswijk, The Netherlands in January 2007. Asexual reproduction of the new *Phalaenopsis* plant by meristem tissue culture since 2011 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Sep. 13, 2016. 'PHALDILEP' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALDILEP' as a new and distinct variety of *Phalaenopsis* plant.

1) White flowers with a small purple center and dark purple lip;
2) 1 to 3 peduncles;
3) Peduncle is medium long and sturdy; and
4) Shape of the leaf is oblong.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs were taken in a greenhouse in Bleiswijk, The Netherlands, from 50-week old plants in October 2016. Colors in the photographs may differ from the color values cited in the detailed botanical description, which accurately describe the actual colors of the new variety.

DESCRIPTION OF THE NEW VARIETY

Figure 1:
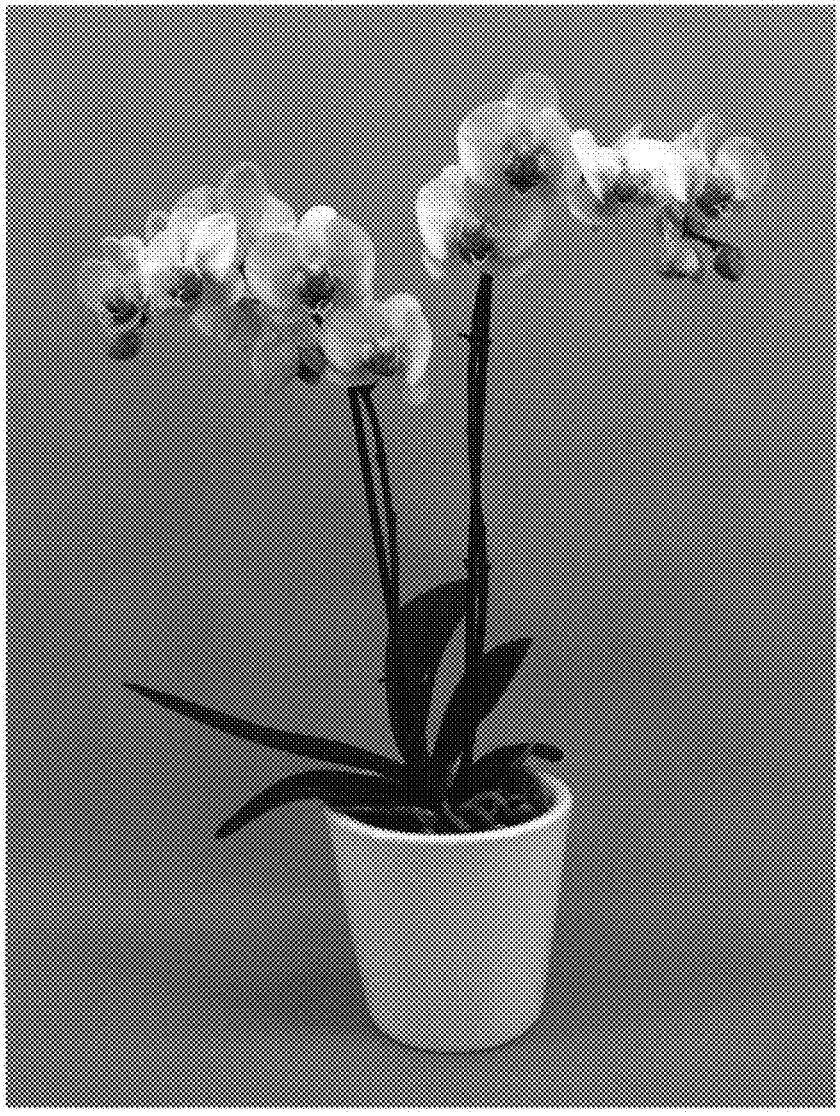
FIG. 1 shows the overall plant habit, including blooms, buds and foliage of 'PHALDILEP'.
Figure 2:
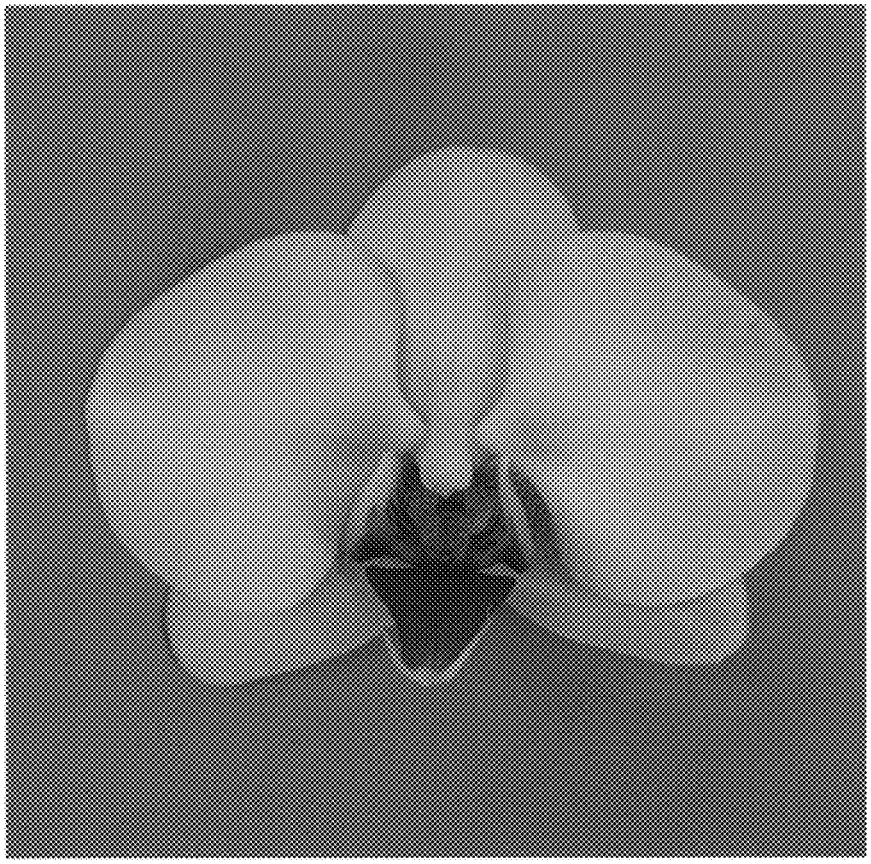
FIG. 2 shows a close-up of a flower of 'PHALDILEP'.
Figure 3:
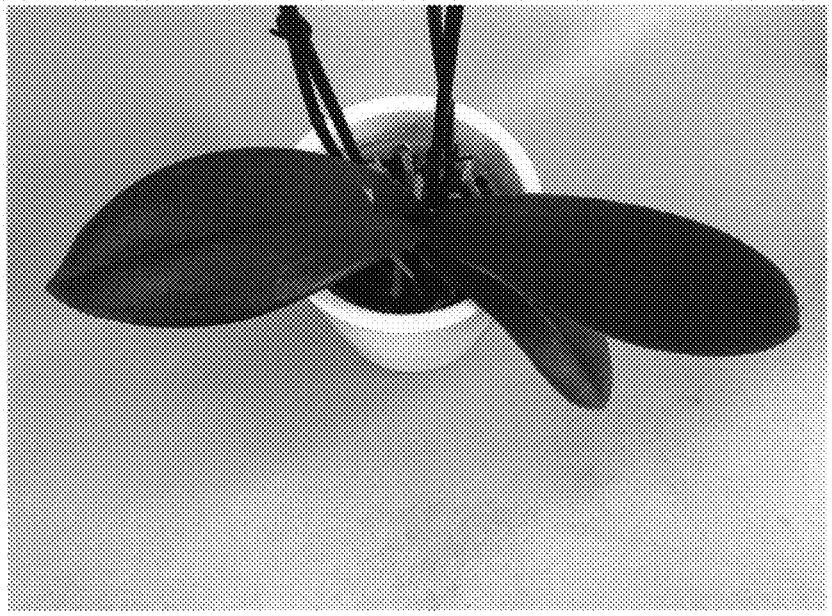
FIG. 3 shows a close-up of the leaves of 'PHALDILEP'.

The following detailed description sets forth the distinctive characteristics of 'PHALDILEP'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in October 2016 on 50-week old plants which were planted from a nursery tray in 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALDILEP'.

Parentage:

*Female parent*.—*Phalaenopsis* cultivar '01-1401' (unpatented).

*Male parent*.—*Phalaenopsis* cultivar '01-1402' (unpatented).

Propagation:

*Type*.—Meristem tissue culture.

Roots:

*Root description*.—Greyed-green (RHS 190B/C) colored roots with green (RHS 146C) and diluting purple (RHS N77A) colored root tips (The exact shades of the roots may vary with minimal changes of environmental conditions, such as root moisture or location inside or outside of the pot).

Plant:

*Commercial crop time to flowering*.—Approximately 48 to 50 weeks from a rooted cutting to finish in a 12 cm pot.

*Growth habit of peduncle*.—Standard, green leaves, raceme to panicle.

*Height (from soil level to top of inflorescence)*.—Approximately 43.0 cm to 53.0 cm.

*Width (measured from leaf tips)*.—About 26.0 cm to 31.0 cm.

*Vigor*.—Strong.

Leaves:

*Mature leaves*.—Quantity per plant: 6 to 8 leaves are produced before flowering. Length (fully expanded): 16.0 cm to 19.0 cm. Width: 6.0 cm to 7.0 cm Shape: Oblong. Base shape: Moderately elongated. Apex: Unequal obtuse. Leaf blade angle with the petiole (measured from the horizontal position): Between 20 degrees and 35 degrees. Leaf margin: Entire. Color: Upper surface: RHS 147A. Lower surface: RHS 147B. Texture: Upper surface: Rough. Lower surface: Smooth. Thickness: 3.0 mm to 3.2 mm. Variegation: Absent. Venation: Pattern: Parallel. Color of the midvein: Upper surface: RHS 147A. Lower surface: RHS 147B.

Peduncle:

*Quantity per plant*.—1 to 3.

*Number of flowers per peduncle*.—13 to 18.

*Length*.—41.0 cm to 51.0 cm.

*Diameter*.—5.7 mm to 5.9 mm.

*Strength*.—Strong.

*Aspect*.—Upright to slightly pendant.

*Texture*.—Smooth.

*Color*.—Mix of green (RHS 147B) and brown (RHS 200B).

*Internode length*.—35.0 mm to 45.0 mm.

*Callosities*.—None.

Inflorescence description:

*Appearance*.—Upright to slightly pendant, raceme to panicle inflorescence with bilaterally symmetrical flowers that open in succession beginning with the lowermost flower.

*Number of inflorescences*.—1 to 3.

*Inflorescence size*.—Height (from base to tip): 170.0 mm to 210.0 mm.

*Flowering time*.—First flowers can be expected 10 to 11 months after planting in a 12 cm (diameter) pot.

*Flower*.—Height: 76.0 mm to 78.0 mm. Diameter: 81.0 mm to 83.0 mm. Depth of lip: 22.0 mm to 24.0 mm.

*Flower longevity*.—On the plant: 8 to 10 weeks.

*Fragrance*.—Absent.

*Flower bud*.—Length: 26.0 mm to 28.0 mm. Width: 21.0 mm to 23.0 mm. Shape: Egg shaped. Color: Light green (RHS 145C) and light purple (RHS N75B).

*Petals*.—Arrangement: Open/free. Shape: Semi-circular. Apex: Rounded asymmetric. Margin: Entire. Length (from base to tip): 37.0 mm to 39.0 mm. Width: 45.0 mm to 47.0 mm. Position of broadest part of petal: Toward the base. Color (when fully opened): Upper surface: Basic color: White (RHS NN155C). Over color: Purple (RHS N75B) at the base and slightly at the edge. Lower surface: Basic color: White (RHS NN155C). Over color: Purple (RHS N75D).

*Dorsal sepal*.—Shape: Elliptic. Apex: Slightly emarginated symmetric. Margin: Entire. Length (from base to tip): 39.0 mm to 41.0 mm. Width: 29.0 mm to 31.0 mm. Color (when fully opened): Upper surface: Basic color: White (RHS NN155C). Over color: Slightly light purple (RHS N75D) at the edge. Lower surface: Basic color: Lilac (RHS 76B). Over color: Purple (RHS N78D) and light green (RHS 145D).

*Lateral sepals*.—Shape: Ovate. Apex: Obtuse asymmetric. Margin: Entire. Length (from base to tip): 41.0 mm to 43.0 mm. Width: 25.0 mm to 27.0 mm. Color (when fully opened): Upper surface: Basic color: White (RHS NN155C). Over color: Light purple (RHS N75D) edge and light green (RHS 145D) spotted (RHS N79B). Lower surface: Basic color: Purple (RHS N75A and N75D). Over color: Light green (RHS 145C).

*Labellum (lip)*.—Whiskers: Present. Length of whiskers: 11.0 mm to 13.0 mm. Color of whiskers: White (RHS NN155C). Pubescence on the lip: Absent.

*Lateral lobe*.—Shape: Spatulate. Margin: Slightly undulated. Length (from base to tip): 16.0 mm to 18.0 mm. Width: 13.0 mm to 15.0 mm. Color: White (RHS NN155C); yellow (RHS 7A) on one side and dark red-purple on the side and stripes at the base (RHS 183A).

*Apical lobe*.—Shape: Triangular. Margin: Entire. Length: 19.0 mm to 21.0 mm. Width: 19.0 mm to 21.0 mm. Color: Dark red (RHS 185A) at the base; purple (RHS N78C) and white (RHS NN155C) towards the whiskers.

*Callus*.—Average size: Medium to large. Height: 0.7 cm to 0.8 cm. Length: 0.7 cm to 0.8 cm. Width: 0.4 cm to 0.5 cm. Color: Yellow (RHS 13A) and spotted (RHS 183A).

*Reproductive organs*.—Column: Length: 8.0 mm to 10.0 mm. Diameter: 5.4 mm to 5.6 mm. Color: White (RHS NN155C). Pollinia: Quantity: 2. Diameter: 1.0 mm to 1.2 mm. Color: Orange (RHS 25A). Ovary: Length: 8.0 mm to 10.0 mm. Diameter: 2.4 mm to 2.6 mm. Pedicel: Length: 29.0 mm to 31.0 mm. Diameter: 2.7 mm to 2.9 mm. Color: Green (RHS 147C/D) at the base and light green (RHS 75C) towards the flower.

Disease, pest, and stress resistance: No specific resistance or susceptibility observed to pathogens and pests common to *Phalaenopsis*.

Fruit and seeds: Fruit and seed development has not been observed on plants of the new *Phalaenopsis*.

COMPARISON WITH PARENTAL AND COMMERCIAL VARIETIES

The female parent plant of 'PHALDILEP', cultivar '01-1401', is no longer in existence, so a meaningful comparison cannot be made.

'PHALDILEP' differs from the male parent plant '01-1402' in that 'PHALDILEP' has white whiskers and an apical lobe that is dark red at the base with purple and white towards the whiskers, whereas '01-1402' has white whiskers with green-yellow tips and an apical lobe that is red-brown at the base and white towards the whiskers. Additionally, 'PHALDILEP' has flowers with a center pattern, whereas '01-1402' has flowers with an even pattern.

'PHALDILEP' is most similar to the commercial *Phalaenopsis* plants named 'PHALDANCIP' (unpatented) and 'PHALBINZIP' (unpatented). 'PHALDILEP' differs from the commercial variety 'PHALDANCIP' in that 'PHALDILEP' has white whiskers, an evenly colored white column, spotted lateral sepals and flowers with a small center pattern, whereas 'PHALDANCIP' has dark red whiskers, a white and purple column, spotted and striped lateral sepals and flowers with a striped pattern. Additionally, 'PHALDILEP' has shorter whiskers, a narrower apical lobe and narrower petals than 'PHALDANCIP'.

'PHALDILEP' differs from the commercial variety 'PHALBINZIP' in that 'PHALDILEP' has white whiskers, an evenly colored white column, spotted lateral sepals and flowers with a small center pattern, whereas 'PHALBINZIP' has dark red whiskers, a white spotted column, shaded and striped lateral sepals and flowers with a shaded and striped pattern. Additionally, 'PHALDILEP' has longer whiskers, a narrower apical lobe and narrower petals than 'PHALBINZIP'.

I claim:

1. A new and distinct variety of *Phalaenopsis* plant named 'PHALDILEP', substantially as described and illustrated herein.

* * * * *